United States Patent
Olesen et al.

(10) Patent No.: US 10,542,913 B2
(45) Date of Patent: Jan. 28, 2020

(54) APPARATUS AND METHOD FOR MOTION TRACKING IN BRAIN IMAGING

(71) Applicant: Danmarks Tekniske Universitet, Kgs. Lyngby (DK)

(72) Inventors: Oline Vinter Olesen, Brønshøj (DK); Rasmus Larsen, Gentofte (DK); Rasmus R. Paulsen, København K (DK); Liselotte Højgaard, København K (DK)

(73) Assignee: DANMARKS TEKNISKE UNIVERSITET, Kgs. Lyngby (DK)

( * ) Notice: Subject to any disclaimer, the term of this patent is extended or adjusted under 35 U.S.C. 154(b) by 613 days.

(21) Appl. No.: 14/403,458

(22) PCT Filed: May 24, 2013

(86) PCT No.: PCT/EP2013/060747
§ 371 (c)(1),
(2) Date: Nov. 24, 2014

(87) PCT Pub. No.: WO2013/174980
PCT Pub. Date: Nov. 28, 2013

(65) Prior Publication Data
US 2015/0359464 A1    Dec. 17, 2015

Related U.S. Application Data

(60) Provisional application No. 61/651,827, filed on May 25, 2012.

(30) Foreign Application Priority Data

May 25, 2012    (EP) .................................... 12169670

(51) Int. Cl.
*A61B 5/11*    (2006.01)
*G01R 33/48*    (2006.01)
(Continued)

(52) U.S. Cl.
CPC .......... *A61B 5/1114* (2013.01); *A61B 5/0042* (2013.01); *A61B 5/055* (2013.01);
(Continued)

(58) Field of Classification Search
CPC ..... A61B 5/1114; A61B 5/055; A61B 5/0042; A61B 5/1128; A61B 5/721; A61B 6/527;
(Continued)

(56) References Cited

U.S. PATENT DOCUMENTS

2006/0209257 A1    9/2006    Bullwinkel
2008/0317313 A1    12/2008    Goddard et al.
(Continued)

FOREIGN PATENT DOCUMENTS

WO    2007/136745 A2    11/2007
WO    WO2010/066824    *   6/2010   ............... A61B 5/08
(Continued)

OTHER PUBLICATIONS

International Search Report and Written Opinion received for PCT Patent Application No. PCT/EP2013/060747, dated Jun. 25, 2013, 9 pages.
(Continued)

*Primary Examiner* — Peter Luong
(74) *Attorney, Agent, or Firm* — Duane Morris LLP; Gregory M. Lefkowitz; Jason M. Nolan

(57) ABSTRACT

Disclosed is apparatus and method for motion tracking of a subject in medical brain imaging. The method comprises providing a light projector and a first camera; projecting a first pattern sequence (S1) onto a surface region of the subject with the light projector, wherein the subject is positioned in a scanner borehole of a medical scanner, the first pattern sequence comprising a first primary pattern ($P_{1,1}$) and/or a first secondary pattern ($P_{1,2}$); detecting the projected first pattern sequence (S1') with the first camera;
(Continued)

determining a second pattern sequence (S2) comprising a second primary pattern ($P_{2,1}$) based on the detected first pattern sequence (S1'); projecting the second pattern sequence (S2) onto a surface region of the subject with the light projector; detecting the projected second pattern sequence (S2') with the first camera; and determining motion tracking parameters based on the detected second pattern sequence (S2').

14 Claims, 14 Drawing Sheets

(51) Int. Cl.
*A61B 5/00* (2006.01)
*A61B 6/03* (2006.01)
*A61B 5/055* (2006.01)

(52) U.S. Cl.
CPC ............ *A61B 6/037* (2013.01); *G01R 33/481* (2013.01); *G01R 33/4806* (2013.01); *A61B 2576/026* (2013.01)

(58) Field of Classification Search
CPC ..... A61B 6/5264; A61B 6/0492; A61B 6/037; A61B 2576/026; G01R 33/4806; G01R 33/481; G01R 33/56509
See application file for complete search history.

(56) References Cited

U.S. PATENT DOCUMENTS

2009/0039235 A1* 2/2009 MacFarlane ........... G01R 33/28
250/206.1
2012/0253201 A1* 10/2012 Reinhold ............. A61B 5/1113
600/473

FOREIGN PATENT DOCUMENTS

WO 2011/113441 A2 9/2011
WO 2011/113441 A3 2/2012

OTHER PUBLICATIONS

International Preliminary Report on Patentability received for PCT Patent Application No. PCT/EP2013/060747, dated Dec. 4, 2014, 6 pages.
Geng, Jason, "Structured-Light 3D Surface Imaging: A Tutorial", Advances in Optics and Photonics, vol. 3, Mar. 31, 2011, pp. 128-160.
Olesen et al., "Motion Tracking for Medical Imaging: A Nonvisible Structured Light Tracking Approach", IEEE Transactions on Medical Imaging, vol. 31, No. 1, Jan. 2012, pp. 79-87.
Extended European Search Report received for European Patent Application No. 16165766.3, dated Aug. 26, 2016, 7 pages.
Olesen et al., "Structured Light 3D Tracking System for Measuring Motions in PET Brain Imaging", Proc. of SPIE, vol. 7625, 2010, pp. 76250X-1-76250X-11.

* cited by examiner

APPARATUS AND METHOD FOR MOTION TRACKING IN BRAIN IMAGING

CROSS REFERENCE TO RELATED APPLICATIONS

This application is a U.S. National Stage patent application of PCT/EP2013/060747, filed on May 24, 2013, which claims priority to European Patent Application No. 12169670.2, filed on May 25, 2012 and U.S. Provisional Application No. 61/651,827, filed on May 25, 2012, the entire contents of which are incorporated herein by reference.

The present invention relates to a method and apparatus for motion tracking in medical imaging, such as brain imaging, in particular in magnetic resonance imaging (MRI) and/or positron emission tomography (PET). The present method and apparatus may be for motion tracking in positron emission tomography (PET), and combined MRI/PET scanners. The present method and apparatus may be for motion tracking in preclinical MRI and PET scanners.

BACKGROUND OF THE INVENTION

Over the last decade, numerous methods for motion tracking in brain imaging have been developed, but head motion during scanning pertains to be a significant problem causing artefacts and significantly reducing image quality.

Known methods include external tracking systems as well as image based motion tracking and correction. Many external tracking systems use markers attached to the subjects head. This potentially introduces errors and complicates the process of preparing the subject for the scan and therefore reduces the usability in clinical practice. Correspondingly, the image based motion tracking methods developed for medical brain imaging generally suffer from an inability to obtain sufficiently high temporal and spatial resolution at the same time. Further, the high resolution of modern medical scanners (down to tenths of a millimeter for MRI and a few millimeters for PET) set strict requirements to motion tracking systems.

SUMMARY OF THE INVENTION

Thus, there is a need for an improved motion tracking of a subject to improve motion correction of scanning images of medical scanners and in particular of a magnetic resonance (MR) and/or PET scanner.

Further, there is a need for a motion tracking system that simplifies the scanning procedure, e.g. reduces pre-processing of the subject.

Accordingly, a method for motion tracking of a subject in imaging, in particular medical or medical brain imaging, is provided, the method comprising providing a light projector and a first camera and projecting a first pattern sequence (S1) onto a surface region of the subject with the light projector, the first pattern sequence comprising a first primary pattern ($P_{1,1}$) and optionally a first secondary pattern ($P_{1,2}$). The subject may be positioned in the scanning area of a scanner, such as in a scanner borehole of a medical scanner. The method comprises detecting the projected first pattern sequence (S1') with the first camera. Optionally, the method comprises determining a second pattern sequence (S2) comprising a second primary pattern ($P_{2,1}$) based on the detected first pattern sequence (S1'), projecting the second pattern sequence (S2) onto a surface region of the subject with the light projector and detecting the projected second pattern sequence (S2') with the first camera. The method may comprise determining motion tracking parameters based on the detected first pattern sequence (S1') and/or the second pattern sequence (S2').

Further, an apparatus for motion tracking of a subject in imaging, in particular medical or medical brain imaging, is provided, the apparatus comprising a control unit, a light projector comprising a light source and a light modulator, and a first camera. The apparatus is configured for projecting a first pattern sequence (S1) onto a surface region of the subject with the light projector, wherein the subject optionally is positioned in the scanning area of a scanner, such as in a scanner borehole of a medical scanner, the first pattern sequence comprising a first primary pattern ($P_{1,1}$) and optionally a first secondary pattern ($P_{1,2}$) and detecting the projected first pattern sequence (S1') with the first camera. Further, the apparatus may be configured for determining a second pattern sequence (S2) comprising a second primary pattern ($P_{2,1}$) based on the detected first pattern sequence (S1'), projecting the second pattern sequence (S2) onto a surface of the subject with the light projector and detecting the projected second pattern sequence (S2') with the first camera. The apparatus may be configured for determining motion tracking parameters based on the detected first pattern sequence (S1') and/or the second pattern sequence (S2').

It is an advantage of the method and apparatus of the present invention that motion tracking in the submilimeter range is enabled.

It is an important advantage of the method and apparatus of the present invention that markerless motion correction is provided, reducing the requirements for preparation of the subject to be scanned.

The method and apparatus of the present invention enable improved image quality of brain imaging and/or may reduce the memory requirements of the apparatus.

The present invention enables increased tracking speed and/or improved accuracy of the motion tracking parameters, due to the adaptive determination of the pattern sequence and patterns thereof. Thereby it is possible to optimize properties of the projected patterns, e.g. in order to focus on relevant subregions for the motion tracking parameters.

The present invention provides for improved patient security since the patterns of a sequence can be adjusted such that eye regions are excluded from illumination or illuminated with desired pattern subregions.

Further, adaptive determination of second patterns enables optimization of patterns to subregions of particular interest for motion tracking. For example, surface subregion(s) having a large curvature are desired in order to obtain motion information for all directions and angles.

BRIEF DESCRIPTION OF THE DRAWINGS

The above and other features and advantages of the present invention will become readily apparent to those skilled in the art by the following detailed description of exemplary embodiments thereof with reference to the attached drawings, in which.

DETAILED DESCRIPTION OF THE INVENTION

Figure 1:
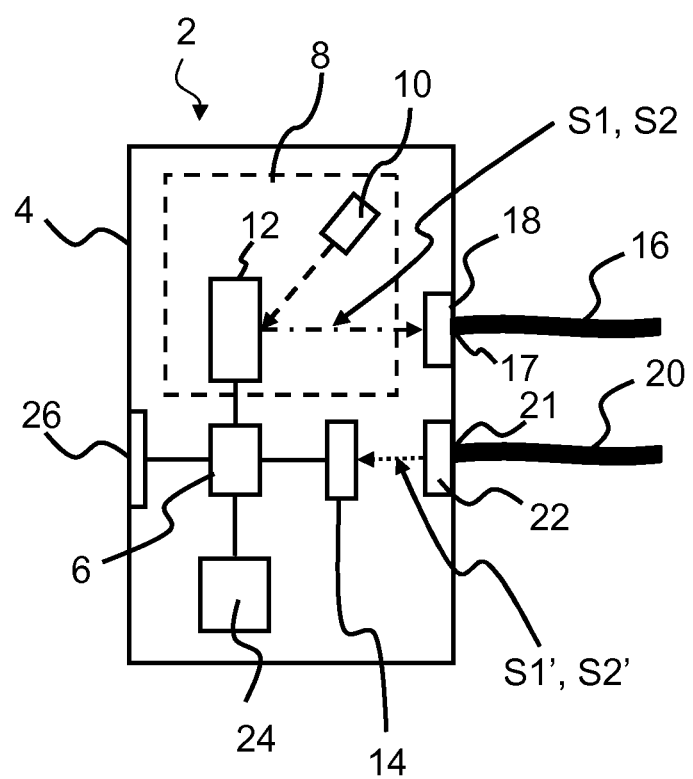
FIG. 1 schematically illustrates an exemplary apparatus according to the invention, FIG. 2 schematically illustrates exemplary positioning of distal ends of optical fibers in a medical scanner.

The figures are schematic and simplified for clarity, and they merely show details which are essential to the understanding of the invention, while other details may have been left out. Throughout, the same reference numerals are used for identical or corresponding parts.

The light projector provided in the method and/or included in the apparatus comprises a light source. The light source may include one or more lasers or LED's including a first laser/LED configured to emit light at a first wavelength $\lambda_1$ and/or a second laser/LED configured to emit light at a second wavelength $\lambda_2$. The light source may include a third laser/LED configured to emit light at a third wavelength $\lambda_3$. The light source may include a broad spectrum light source, such as a metal-halide lamp. In one or more embodiments, the light source may comprise a light emitting diode (LED). The light source may comprise a filter for forming light with desired frequency spectrum/wavelength distribution. In one or more embodiments, the light source may be adapted to emit light in the infrared (IR) or near-infrared (NIR) range, for example at a wavelength in the range from 700 nm to about 1,000 nm, e.g. about 850 nm. In one or more embodiments, the light source may be adapted to emit light in the UV range, The first laser/LED may be a red or orange/red laser, wherein the first wavelength $\lambda_1$ is in the range from about 590 nm to about 700 nm. In one or more embodiments the first wavelength $\lambda_1$ is about 635 nm. The first laser/LED may be an LED, wherein the first wavelength $\lambda_1$ is in the range from about 830 nm to about 870 nm, e.g. about 850 nm.

The second laser/LED may be a green laser, wherein the second wavelength $\lambda_2$ is in the range from about 490 nm to about 560 nm, e.g. about 532 nm. The second laser/LED may be an LED, wherein the second wavelength $\lambda_2$ is in the range from about 880 nm to about 920, e.g. about 900 nm.

The third laser/LED may be a blue or violet laser, e.g. wherein the third wavelength $\lambda_3$ is in the range from 430 nm to about 490 nm, e.g. about 445 nm or about 473 nm. The third laser/LED may be an LED, e.g. wherein the third wavelength $\lambda_3$ is in the range from 930 nm to about 1,000 nm, e.g. about 940 nm.

The light source may comprise a UV source, e.g. configured to emit light with a wavelength in the range from about 230 nm to about 400 nm, e.g. about 350 nm.

The light projector provided in the method and/or included in the apparatus may comprise a light modulator, e.g. for projection of patterns onto the surface region or scene of the subject. The light modulator may comprise a liquid crystal display (LCD) chip or a digital light processing (DLP) chip. In one or more embodiments, the light modulator may comprise a liquid crystal on silicon (LCOS) chip. In one or more embodiments, the light modulator may comprise grids, slits or filters. The light modulator may be a transmitting or reflective light modulator.

The light projector may be connected to the control unit for receiving control signal(s) from the control unit. The control signal(s) may comprise pattern sequence parameters, such as number, configuration, order and/or timing of pattern(s) of the pattern sequence. In one or more embodiments, the control signal(s) may comprise a pattern sequence selector, and the light projector may be configured for projecting different pattern sequences dependent on the pattern sequence selector.

The resolution of the light projector limits the pattern resolution. The light projector may have a resolution of HVGA (480×320 pixels) or more, e.g. (608×684 pixels), SVGA (800×600 pixels), XGA (1024×768 pixels), 720p (1280×720 pixels), or 1080p (1920×1080 pixels).

In one or more embodiments, a number of different pattern sequences may be stored in the light projector, and the light projector may be configured to project a selected pattern sequence based on a pattern sequence selector from a control unit.

A pattern sequence (S), e.g. a first pattern sequence (S1) and/or a second pattern sequence (S2), comprises one or more patterns (P), such as a plurality of patterns including a primary pattern and a secondary pattern. A pattern sequence comprises or consists of a number N of patterns. A pattern sequence may be defined by pattern sequence parameters, for example including number of patterns, configuration/structure of respective patterns, order of patterns and/or timing of pattern(s) of the pattern sequence. The duration of a pattern sequence may be in the range from 1 millisecond to about 1 second. The duration of a pattern sequence may be about 10 milliseconds, about 20 milliseconds, about 50 milliseconds, about 100 milliseconds or about 200 milliseconds.

A pattern may comprise a number of pixels, e.g. arranged in an array along a first and second axis. A pattern may be defined by pattern parameters, e.g. including pixel settings (color/wavelength and/or intensity) of each pixel and/or one or more groups of pixels in the pattern. A group of pixels of a pattern may be referred to as a subregion denoted R of a pattern. Accordingly, a pattern may comprise one or more subregions $R_1, R_2, R_3 \ldots$, a subregion comprising one or more pixels. Pattern sequence parameters may include pattern parameters, e.g. of a primary pattern, a secondary pattern and/or a tertiary pattern.

A pattern, subregions thereof or different pixels of the pattern may be color/wavelength coded, intensity coded, and/or binary coded. For example pixel(s) of a first subregion, e.g. corresponding to the eye region of the subject may be masked out for one or more, e.g. all, patterns of the second pattern sequence such that the eye region is not illuminated.

In one or more embodiments, one or more patterns of the first and/or second pattern sequence are color/wavelength coded, for example by having a varying color along the first axis and a constant or varying color along the second axis.

In one or more embodiments, one or more patterns of the first and/or second pattern sequence are intensity coded, for example by having a varying intensity along the first axis and a constant or varying intensity along the second axis.

In one or more embodiments, one or more patterns of the first and/or second pattern sequence are binary coded, i.e. a pixel or subregions of the pattern is assigned one of "Light" and "No light" to form the desired pattern.

The first pattern sequence denoted S1 comprises a first primary pattern denoted $P_{1,1}$ and optionally a first secondary pattern denoted $P_{1,2}$. The first pattern sequence S1 comprises or consists of a number $N_1$ of patterns, where $N_1$ may be in the range from one to hundred, such as in the range from two to ten. In specific examples, $N_1$ is two, three, four, five or six. In one or more embodiments, $N_1$ is at least ten.

The second pattern sequence denoted S2 comprises a second primary pattern denoted $P_{2,1}$ and optionally a second secondary pattern $P_{2,2}$. The second pattern sequence (S2) comprises or consists of a number $N_2$ of patterns, where $N_2$ may be in the range from one to hundred, such as in the range from two to ten. In specific examples, $N_2$ is one, two, three, four, five or six. In one or more embodiments, $N_2$ is at least ten.

The first camera may be a CCD camera or a CMOS camera. The first camera may have a resolution of at least 640×480, e.g. 1280×960, 3264×2448 or more.

In the method, projection of the first pattern sequence and detection of the projected first pattern sequence may be repeated at least once, such as at least 10 times, at least 50 times, and the second pattern sequence (S2) may be based on the repeated first pattern sequence. In the method, projection of the second pattern sequence may be repeated at least once, such as at least 50 times, or at least 100 times, or at least 144,000 times (2 hours with 20 Hz).

The surface region may have an area of at least 0.1 cm$^2$, e.g. in the range from 1 cm$^2$ to 500 cm$^2$. In one or more embodiments, the surface region area may be in the range from 20 cm$^2$ to 100 cm$^2$.

The surface region may at least partly cover a nasal region of the subject. This may lead to improved motion tracking due to the significant curvature of the subject surface in this region. Further, facial movements are limited near the bridge of the nose which is preferred when tracking the motion of the scull and the brain.

Different patterns may each comprise different colors/wavelengths and/or a subregion of a pattern may comprise a color or wavelength different from another subregion of the respective pattern. Accordingly, the first primary pattern $P_{1,1}$ or subregions $R_{1,1,1}, R_{1,1,2}, R_{1,1,3}, R_{1,1,4}, \ldots$ thereof may comprise light at a first wavelength, i.e. have a first color coding, and/or the first secondary pattern ($P_{1,2}$) or subregions $R_{1,2,1}, R_{1,2,2}, R_{1,2,3}, R_{1,2,4}, \ldots$ thereof may comprise light at a second wavelength, i.e. have a second color coding.

The method may comprise determining whether the current pattern sequence should be recalculated or not. If YES, the pattern sequence may move to determining a new pattern sequence including determining the second pattern sequence in a first cycle. If NO, the method may proceed with projecting and detecting the current pattern sequence.

In the method, determining the second pattern sequence may comprise determining second pattern(s) such that projection of light onto the eye region of the subject during projection of the second pattern sequence is limited or substantially eliminated. Thereby improved patient security is provided since the patterns of a sequence can be adjusted such that the eye region is excluded from illumination.

In the method, determining the second pattern sequence may comprise identifying position parameters of a first region and/or a second region of the surface region. The first region may have desired first curvature properties. The first region may at least partly cover the nasal region of the subject and/or the second region may be an eye region covering one or both eyes. Determining pattern parameters of the second pattern sequence, e.g. second primary pattern parameters of the second primary pattern ($P_{2,1}$) and/or second secondary pattern parameters of the second secondary pattern ($P_{2,2}$), may be based on the position parameters of the first region and/or the second region. For example, an optimum pattern configuration may be applied to a first subregion of one or more of the patterns of the second pattern sequence, the first subregion corresponding to the first region and/or a subregion of one or more patterns of the second pattern sequence may be blocked or masked out to avoid undesired illumination of the second region.

The second pattern sequence (S2) may be given as:

$$S2=f(S1,S1'),$$

where S1 is the first pattern sequence or pattern(s) thereof, and S1' is the detected first pattern sequence or pattern(s) thereof.

Determining the second pattern sequence (S2) may comprise determining second pattern(s) ($P_{2,1}, P_{2,2}, \ldots, P_{2,N2}$) such that detection of a desired second pattern sequence ($\underline{S2}'$) can be expected or is aimed at. A desired detected second pattern sequence ($\underline{S2}'$) may comprise one or more desired detected second patterns ($\underline{P}'_{2,1}, \underline{P}'_{2,2}, \ldots, \underline{P}'_{2,N2}$) that require less image processing for facilitating a faster/improved motion correction. Accordingly, the second pattern sequence may be given as:

$$S2=f(S1,S1',\underline{S2}'),$$

where S1 is the first pattern sequence or pattern(s) thereof, S1' is the detected first pattern sequence or pattern(s) thereof, and $\underline{S2}'$ is the desired detected second pattern sequence or pattern(s) thereof.

A pattern P of a pattern sequence S, such as a first pattern of the first pattern sequence S1 and/or a second pattern of the second pattern sequence S2, may comprise one or more line segments, such as one or more straight line segments. A line segment may be curved. Line segments L of a pattern may have the same or varying length. Line segments L of a pattern may have the same or varying width. Line segments of a pattern may be parallel or angled with respect to each other, such as perpendicular. Line segments of different patterns within the same pattern sequence may be perpendicular or parallel, e.g. a primary pattern may comprise one or more straight line segments perpendicular or otherwise angled with respect to one or more straight line segments of a secondary pattern. A pattern may comprise curved and angled lines or line segments in such a way that the pattern is detected or seen as straight lines from the camera perspective.

Determination of second pattern sequence may comprise determining size and/or shape of subregions or line segment(s) of patterns in the second pattern sequence.

Determination of second pattern sequence may comprise determining position of subregions or line segment(s) of patterns in the second pattern sequence.

Determining a second pattern sequence may be based on a desired detected second pattern sequence comprising one or more desired detected patterns.

Determination of second pattern sequence may comprise determining duration $T_2$ of the second pattern sequence where $T_2$ is less than the duration $T_1$ of the first pattern sequence.

Determination of second pattern sequence may comprise reducing the illuminated area of second patterns of the second pattern sequence in order to reduce light interference due to light scatter. Thereby image quality of detected sequences is improved leading to more accurate motion tracking. Further, tailoring or determining patterns by reducing the illuminated pattern area may reduce the memory requirements of the system and/or enables improved utilization of the available memory.

Determination of second pattern sequence may comprise increasing the illuminated area of second patterns of the second pattern sequence in order to optimize image projection and/or detection, for example if a first pattern sequence does not provide sufficient resolution/accuracy. Thereby image quality of detected sequences is improved leading to more accurate motion tracking. Further, tailoring or determining patterns by increasing the illuminated pattern area may provide improved motion correction accuracy.

Determining motion tracking parameters may be based on calculation of default position parameters of the subject. The default position parameters may be calculated based on the detected first pattern sequence(s) (S1') and/or the detected second pattern sequence(s) (S2').

The method may comprise sending the motion tracking parameters or selected motion tracking parameters to the medical scanner or a control unit for motion correction of the scanning images. The motion tracking parameters may be sent during the scanning procedure and/or after the scanning procedure. The motion tracking parameters may be stored in a database or memory.

Determining motion tracking parameters may comprise generating a 3D point cloud representation of the surface region or parts thereof. Motion tracking parameters may be estimated or determined by aligning point clouds of the 3D point cloud representation to a reference surface. The reference surface may be based on calculation of default position parameters of the subject.

Determining motion tracking parameters may be based on the first pattern sequence (S1). Additionally, or alternatively, determining motion tracking parameters may be based on the detected first pattern sequence (S1').

Determining motion tracking parameters may be based on the second pattern sequence (S2).

Determining motion tracking parameters may be based on a 3D model of the surface region of the subject. This may lead to simplified determination of MTP's.

Dynamic configuration or determination of the second pattern sequence based on a first pattern sequence enables improved tracking of the subject using less data, since pattern sequences are tailored to the specific subject to be scanned. Thus, the image data quality is improved which in turn reduces the demands for memory and/or processing capacity.

Further, dynamic configuration or determination of the second pattern sequence based on a first pattern sequence enables simplified determination of motion tracking parameters (MTP), since pattern sequences may be tailored to the specific surface region geometry to be scanned, allowing faster and/or more accurate tracking of motion.

The apparatus comprises a control unit. The control unit is connected to the light projector for sending and/or receiving control signals from/to the light source. The control signals to the light source may comprise pattern sequence parameters. Further, the control unit is connected to the first camera for receiving pattern sequence data. The control unit may be configured to send and/or receive control signals to/from the first camera.

The control unit, the light projector, and the first camera may be accommodated in a housing. The apparatus may comprise a first coupling device for optically coupling light from the light projector to first optical fibers. The apparatus may comprise a second coupling device for optically coupling light from second optical fibers to the first camera. The first and/or the second optical fibers may be optional, i.e. the method and apparatus may be used without the optical fibers.

The apparatus may comprise a user interface connected to the control unit. The user interface may comprise one or more connectors, e.g. for connecting the apparatus to an external computer or a medical scanner.

The apparatus may comprise memory, e.g. configured for storing pattern sequence parameters including pattern parameters. Motion tracking parameters may be stored in the memory. In one or more embodiments, the apparatus is configured to determine and send motion tracking parameters in real-time to an external computer or a medical scanner. This may reduce the demands on memory size.

The control unit may comprise a processor adapted for determining the second pattern sequence.

The apparatus may comprise first optical fibers having proximal ends optically coupled to the light projector for projecting at least one pattern from the light projector via the first optical fibers onto the surface region of the subject positioned in a borehole of the medical scanner. The first optical fibers may comprise at least 100 optical fibers, such as at least 10,000 fibers, each fiber corresponding to a pixel in a pattern projected onto the surface region of the subject. In one or more embodiments, the number of first optical fibers is equal to or larger than the number of pixels in the light projector, for full benefit of the light projector resolution. The first optical fibers have distal ends. The apparatus may comprise a first optical element, such as a first lens or a first lens assembly, arranged at the distal end of the first optical fibers for coupling pattern sequences from the first optical fibers to the surface region of the subject. The number of first optical fibers may match or be in the range of ±20% of the resolution of the light projector.

The apparatus may comprise second optical fibers having proximal ends optically coupled to the first camera for detecting the at least one projected pattern via the second optical fibers. The second optical fibers may comprise at least 100 optical fibers, such as at least 100,000 fibers. Each second optical fiber may correspond to one or more pixels in the first camera. In one or more embodiments, the number of second optical fibers is equal to or larger than the number of pixels in the light projector for full benefit of the light projector resolution. The second optical fibers have distal ends. The apparatus may comprise a second optical element, such as a second lens or a second lens assembly, arranged at the distal end of the second optical fibers for coupling pattern sequences from the surface region of the subject to the second optical fibers. The number of second optical fibers may match or be in the range of ±20% of the resolution of the first camera.

The first and second optical fibers may be arranged in respective first and second fiber arrays.

In one or more embodiments, the first optical fibers comprise a first array of 400×400 or 600×600 fibers or 680×480 fibers. In one or more embodiments, the second optical fibers comprise a second array of at least 400×400 or 600×600 fibers or 680×480 fibers. The optical fibers may be arranged in an array of any suitable size and shape, e.g. rectangular, circular, oval, polygonal or others.

Using first and second optical fibers enables or facilitates the use of the method and apparatus for medical scanners with a permanent magnetic field surrounding the object, e.g. an MR scanner. Further, using first and second optical fibers enables or facilitates the use of the method and apparatus for medical scanners with limited access to the subject due to the subject being positioned in a scanner borehole during scanning.

The apparatus may comprise a second camera for detecting the first and/or the second pattern sequence.

The medical scanner may be a magnetic resonance (MR) scanner. Further, the method and apparatus for motion tracking may be employed for motion correction of scanning images obtained by other medical scanners, such as a positron emission tomography (PET) scanner, a single photon emission computed tomography (SPECT) scanner or a computed tomography (CT) scanner. In one or more embodiments, the method and apparatus may be employed for motion correction of a subject in a combined PET-MR scanner or a combined PET-CT scanner.

FIG. 1 schematically shows an apparatus to the present invention. The apparatus 2 comprises a housing 4 accommodating a control unit 6 and a light projector 8 comprising a light source 10 and a light modulator 12. Further, the apparatus 2 comprises a first camera 14 connected to the control unit 6 for exchange of control signals and/or pattern sequence data between the control unit and the first camera. During use, first optical fibers 16 are coupled to the apparatus at the proximal ends 17 of the first optical fibers via first optical coupler 18 such that light from the light projector 8 is coupled into the first optical fibers 16. The first optical fibers 16 may be fixedly mounted to the housing, i.e. the first optical fibers may form a part of the apparatus. During use, second optical fibers 20 are coupled to the apparatus at the proximal ends 21 of the second optical fibers via second optical coupler 22 such that pattern sequences projected on the surface region is detected by the first camera 14. The first and second optical fibers may be fixedly mounted to the housing 4, i.e. the first and second optical fibers may form a part of the apparatus, thereby simplifying setting up the apparatus. In one or more embodiments, the first optical fibers are provided with a connector at the proximal end for releasably coupling the first optical fibers to the apparatus. In one or more embodiments, the second optical fibers are provided with a connector at the proximal end for releasably coupling the second optical fibers to the apparatus.

The apparatus 2 is configured for projecting a first pattern sequence (S1) onto a surface region of the subject with the light projector 10, wherein the subject is positioned in a scanner borehole of a medical scanner, the first pattern sequence comprising a first primary pattern ($P_{1,1}$) and a first secondary pattern ($P_{1,2}$) and detecting the projected first pattern sequence (S1') with the first camera 14. The control unit determines a second pattern sequence (S2) comprising a second primary pattern ($P_{2,1}$) based on the detected first pattern sequence (S1') and sends control signals to the light projector 10 projecting the second pattern sequence (S2) onto a surface of the subject. The projected second pattern sequence (S2') is detected with the first camera and the pattern sequence data are processed in the control unit and/or in the first camera. Upon or during detection of pattern sequence data, the apparatus 2 determines motion tracking parameters based on the detected second pattern sequence (S2').

Figure 2:
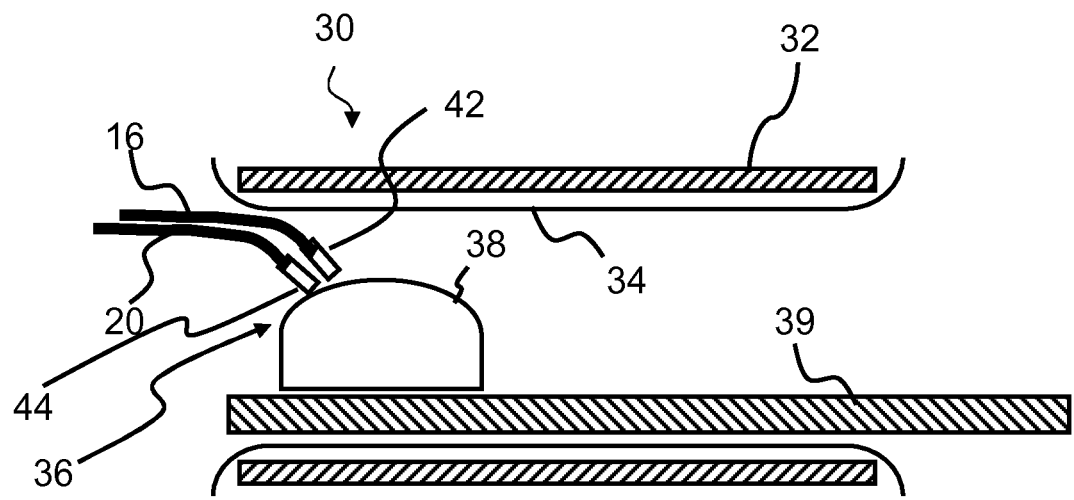

FIG. 2 schematically illustrates a medical scanner for use with the method and apparatus. The scanner 30 is an MR scanner comprising a permanent magnet 32 in a scanner housing 34 forming a scanner borehole 36. The scanner 30 comprises a head coil 38 for scanning a subject positioned on the support structure (scanner bed) 39. Distal ends 42, 44 of the respective optical fibers 16, 20 are positioned in the scanner borehole 36 for projecting and detecting pattern sequences on/from a surface region within the head coil 38.

Figure 3:
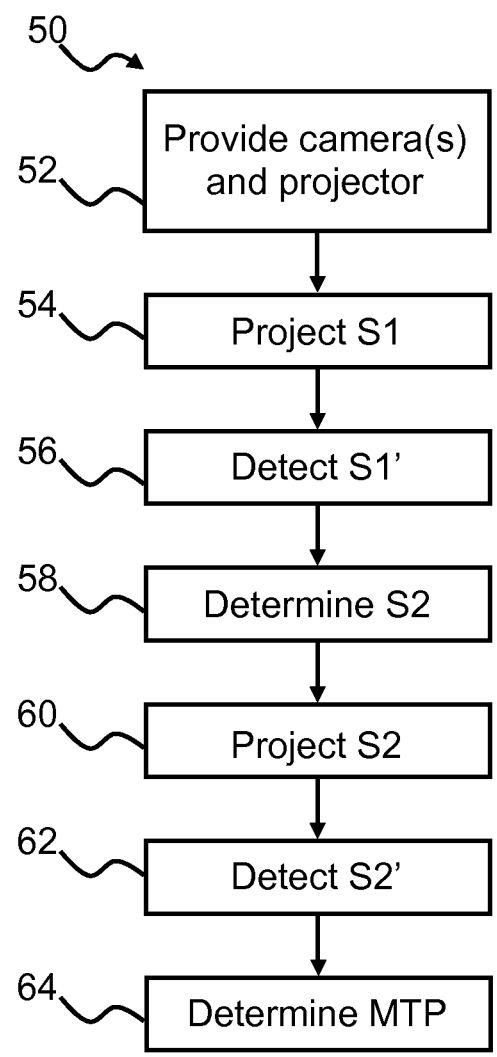
FIG. 3 illustrates an exemplary method according to the present invention.

FIG. 3 illustrates an exemplary method according to the invention. A method 50 for motion tracking of a subject in medical brain imaging is illustrated. The method 50 comprises providing 52 a light projector and a first camera and projecting 54 a first pattern sequence S1 onto a surface region of the subject with the light projector. The subject is positioned in a scanner borehole of a medical scanner (see FIG. 2) and the first pattern sequence S1 comprises a first primary pattern $P_{1,1}$ and a first secondary pattern $P_{1,2}$. The method 50 comprises detecting 56 the projected first pattern sequence (S1') with the first camera. Further, the method 50 comprises determining 58 a second pattern sequence S2 comprising at least a second primary pattern $P_{2,1}$ based on the detected first pattern sequence S1' and projecting 60 the second pattern sequence S2 onto a surface region of the subject with the light projector. The method 50 also comprises detecting 62 the projected second pattern sequence S2' with the first camera and optionally determining 64 motion tracking parameters (MCP) based on the detected second pattern sequence S2'. In the method 50 the second pattern sequence S2 comprises at least two different patterns including a second secondary pattern $P_{2,2}$. The method 50 may be performed using the apparatus 2 shown in FIG. 1, In one or more embodiments of the method, 58, 60, and 62 may be omitted.

Figure 4:
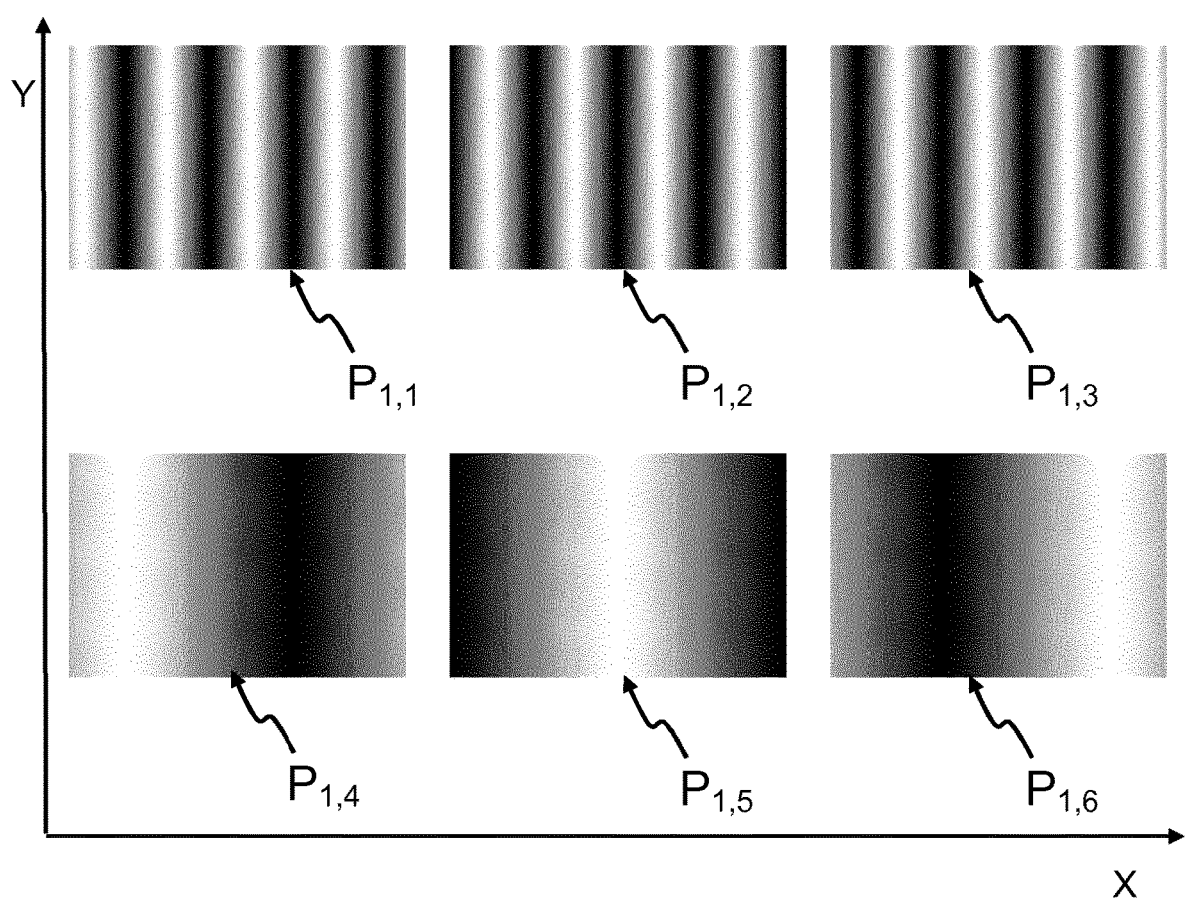
FIG. 4 illustrates exemplary patterns of a first pattern sequence.

FIG. 4 illustrates patterns of an exemplary first pattern sequence comprising six different patterns $P_{1,1}$, $P_{1,2}$, $P_{1,3}$, $P_{1,4}$, $P_{1,5}$ and $P_{1,6}$. The patterns are intensity coded by varying the intensity of pixels along the first axis X.

Figure 5:
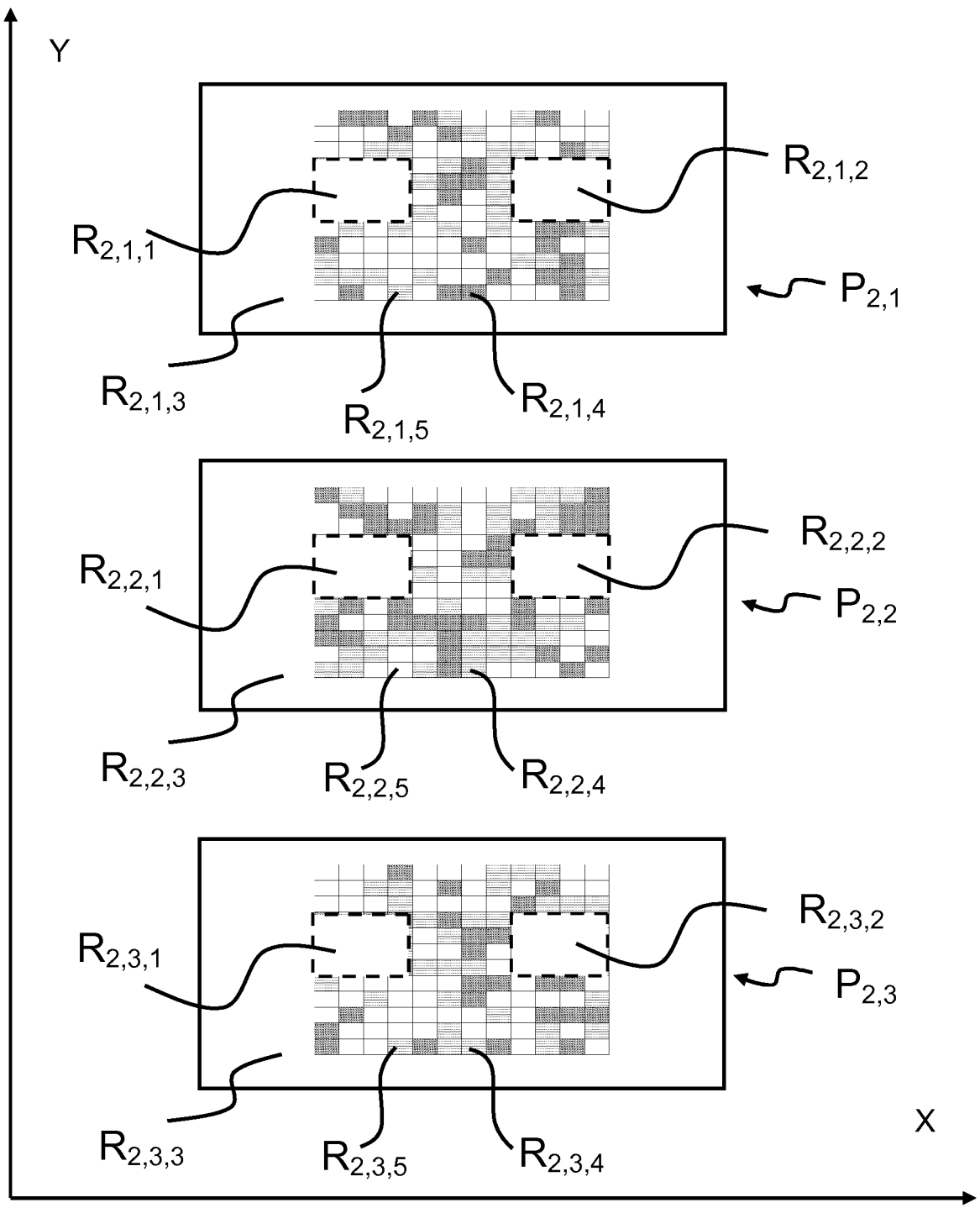
FIG. 5 illustrates exemplary patterns of a second pattern sequence.

FIG. 5 illustrates patterns of an exemplary second pattern sequence S2 determined based on a projected first pattern sequence. The second pattern sequence consists of or comprises three second patterns $P_{2,1}$, $P_{2,2}$, $P_{2,3}$. In the second primary pattern $P_{2,1}$, a first subregion $R_{2,1,1}$ corresponding to a first eye region of the subject has been masked out, i.e. no light or substantially no light is projected in the first subregion $R_{2,1,1}$ of the second primary pattern. Further, a second subregion $R_{2,1,2}$ corresponding to a second eye region of the subject has been masked out, i.e. no light or substantially no light is projected in the second subregion $R_{2,1,2}$ of the second primary pattern. Further, a third subregion $R_{2,1,3}$ corresponding to a region of the surface region of the subject where the curvature is small and thus provide tracking data of low quality has been masked out, i.e. no light or substantially no light is projected in the third subregion $R_{2,1,1}$ of the second primary pattern. It may be desired to reduce the illuminated area of a pattern in order to reduce light interference due to light scatter. Thereby image quality is improved leading to more accurate motion tracking. Further, tailoring or determining patterns by reducing the illuminated pattern area may reduce the memory requirements of the system and/or enables improved utilization of the available memory. Subregions $R_{2,1,4}$ and $R_{2,1,4}$ may be determined based on the detected first pattern sequence.

The size and shape of subregions of second patterns are selected based on the first pattern sequences S1, S1'.

Figure 6:
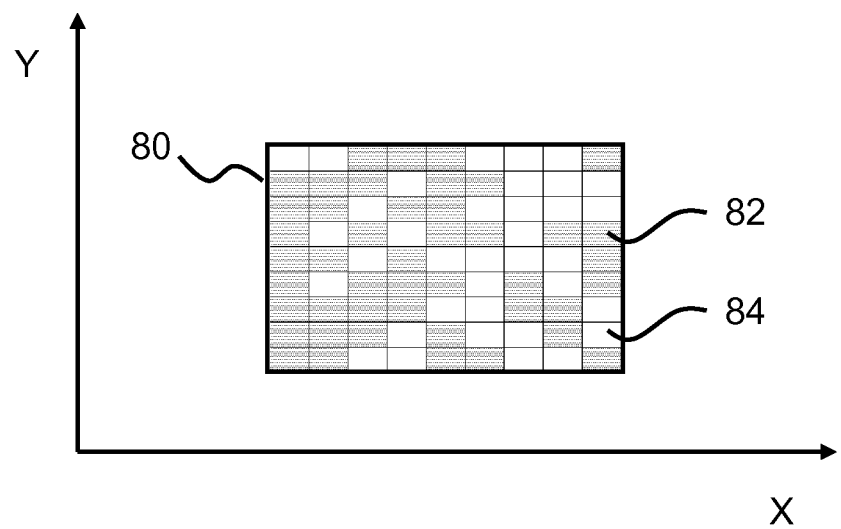
FIG. 6 illustrates an exemplary subregion of a pattern.
Figure 7:
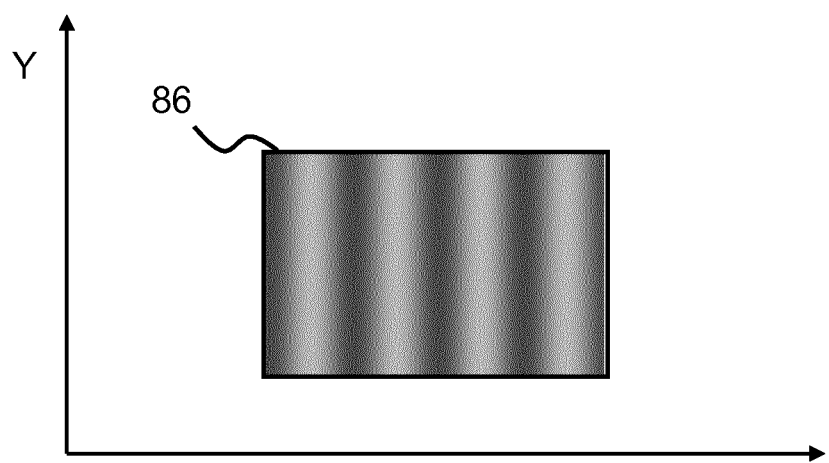
FIG. 7 illustrates an exemplary subregion of a pattern.
Figure 8:
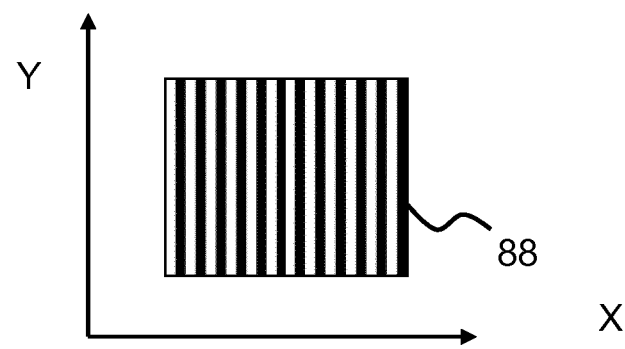
FIG. 8 illustrates an exemplary subregion of a pattern.
Figure 9:
FIG. 9 illustrates an exemplary subregion of a pattern.
Figure 10:
FIG. 10 illustrates an exemplary subregion of a pattern, FIG. 11 schematically illustrates a control unit.

FIG. 6 shows an exemplary subregion 80 of a pattern $P_{2,1}$ of the second pattern sequence. The subregion 80 has 9×9 pixels and each pixel is coded with a color and/or intensity. The intensity may binary coded, e.g. where "1" means "light" and "0" means "no light". For example, the pixel 82 may be coded with light at first wavelength (e.g. red light) and pixel 84 may be coded with intensity zero or "no light" as illustrated.

FIGS. 7-10 illustrate exemplary subregions of a pattern. The subregion 86 is color coded with varying color along the first axis X and the same color along the second axis Y. The subregion 88 is binary coded with a striped pattern, i.e. varying coding along the first axis and constant coding along the second axis Y. Subregions 90, 92 are binary coded with different number of pixels in each subregion.

Figure 11:
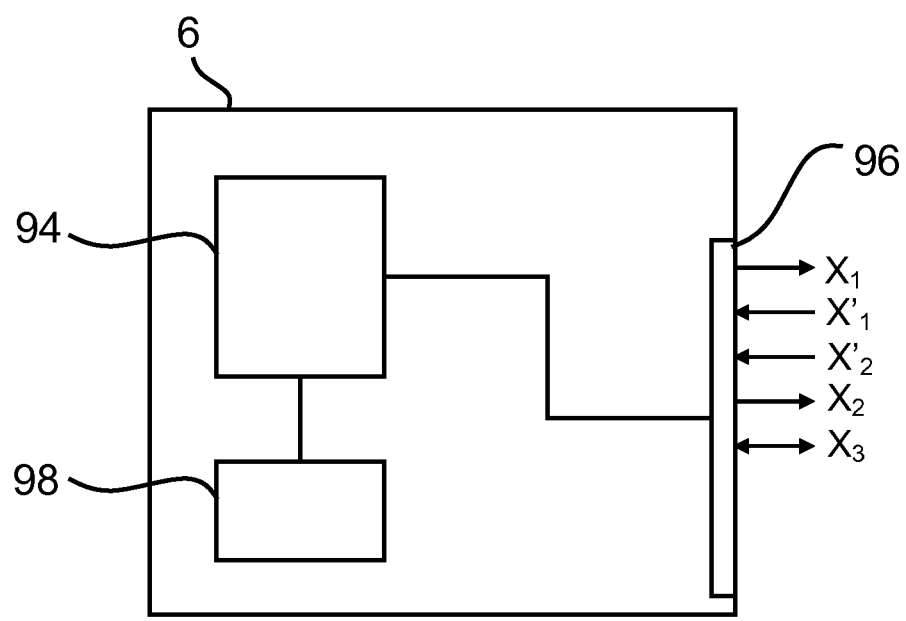

FIG. 11 shows an exemplary control unit 6 comprising a processor 94 connected to interface 96 with connectors for connecting the control unit to other units of the apparatus. The control unit 6 is configured to send control signal(s) $X_1$ to the light projector for controlling the light projector. Optionally, the control unit 6 is configured to receive control signal(s) $X_1'$ from the light projector. The control signal $X_1$ is indicative of pattern sequence configuration and/or pattern sequence timing. Optionally, the control unit 6 is configured to send control signal(s) $X_2$ to the first camera for controlling the first camera. The control unit 6 is configured to receive control signal(s) $X_2'$ from the first camera. The control signals $X_2'$ may comprise pattern sequence data or images detected with the first camera, e.g. first pattern sequence data for determining a second pattern sequence in the processor. The control unit 6 may be configured to store and/or retrieve data $X_3$ from a memory of the apparatus. The control unit 6 may comprise an internal memory 98 connected to the processor.

Figure 12A:
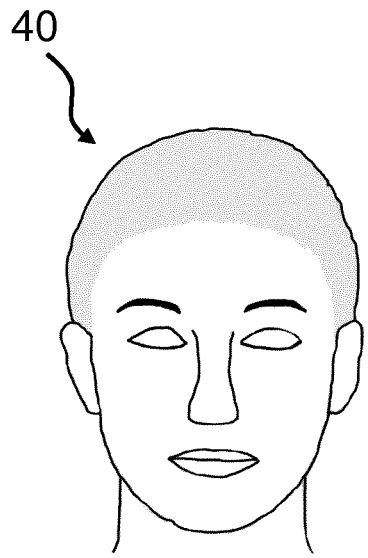
FIG. 12A-D illustrates exemplary projected patterns on a subject.
Figure 12B:
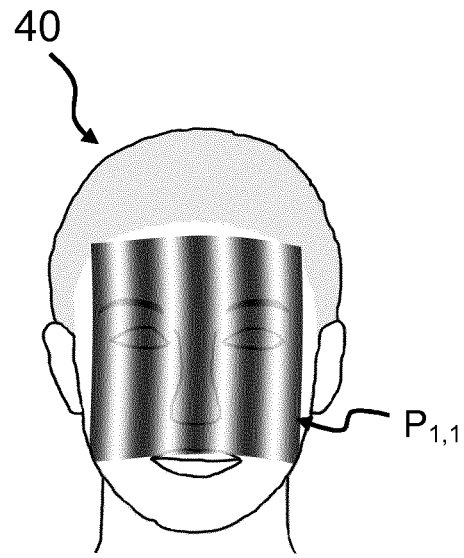
Figure 12C:
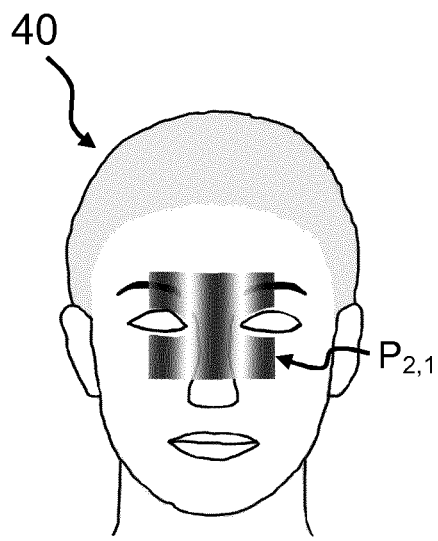
Figure 12D:
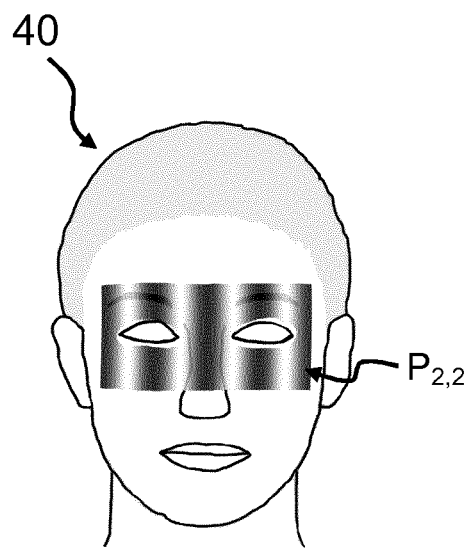

FIGS. 12A-D illustrate a subject with exemplary projected patterns. In FIG. 12A, the subject 40 is shown without projected pattern. FIG. 12B illustrates the subject with a first primary pattern $P_{1,1}$ projected and FIGS. 12C and 12D illustrates the subject with a second primary pattern $P_{2,1}$ and a second secondary pattern $P_{2,2}$ of a second pattern sequence. The patterns $P_{2,1}$ and $P_{2,2}$ are determined based on a detection $P'_{1,1}$ or capture of the first primary pattern $P_{1,1}$ with the first camera.

Figure 13:
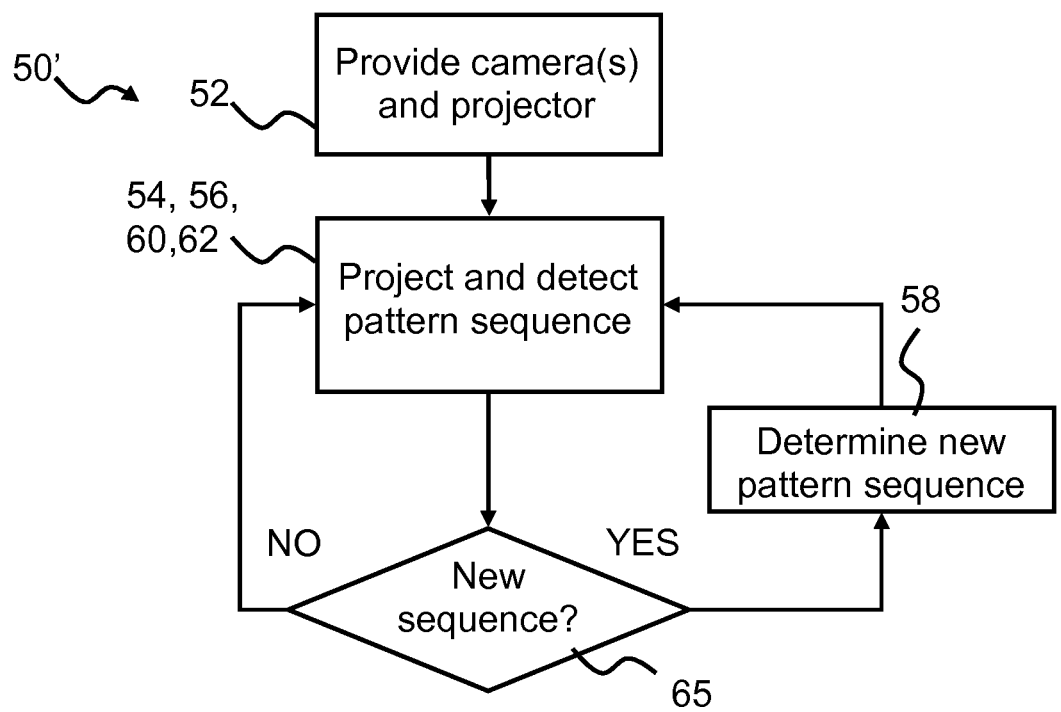
FIG. 13 illustrates an exemplary method according to the present invention, FIG. 14 schematically illustrates exemplary positioning of the distal ends of optical fibers in a medical scanner, FIG. 15 schematically illustrates exemplary positioning of the distal ends of optical fibers in a medical scanner.

FIG. 13 illustrates at least a part of an exemplary method 50' of the present invention. In the method 50' projecting and detecting the first sequence is repeated at least once, for example at least ten times. The method may comprise deciding 65 whether the current pattern sequence should be recalculated. If YES, the method proceeds to determining a new pattern sequence 58 (the second pattern sequence in the first cycle) and proceeding to projecting and detecting the new pattern sequence. If NO, the method proceeds to projecting and detecting the current pattern sequence. The pattern sequence may be recalculated (YES), if the image quality of the detected pattern sequence does not fulfil a quality criterion.

Figure 14:
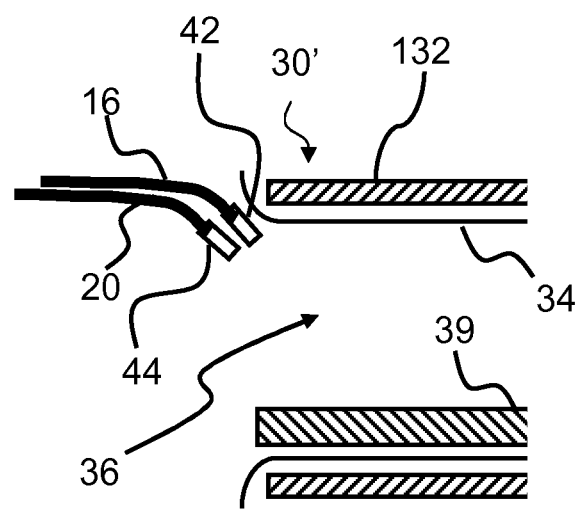

FIG. 14 schematically illustrates a medical scanner for use with the method and apparatus. The scanner 30' is a PET scanner comprising at least one detector ring 132 in a scanner housing 34 forming a scanner borehole 36. The scanner 30' comprises a head coil 38 for scanning a subject positioned on the support structure (scanner bed) 39. Distal ends 42, 44 of the respective optical fibers 16, 20 are positioned outside the detector ring 132 and near the scanner borehole 36 for projecting and detecting pattern sequences on/from a surface region within the scanner borehole 36. Optionally, distal ends 42, 44 are provided with respective first and second lens assemblies. The optical fibers may be omitted in the apparatus for the PET scanner by positioning the apparatus similar to the distal ends 42, 44.

Figure 15:
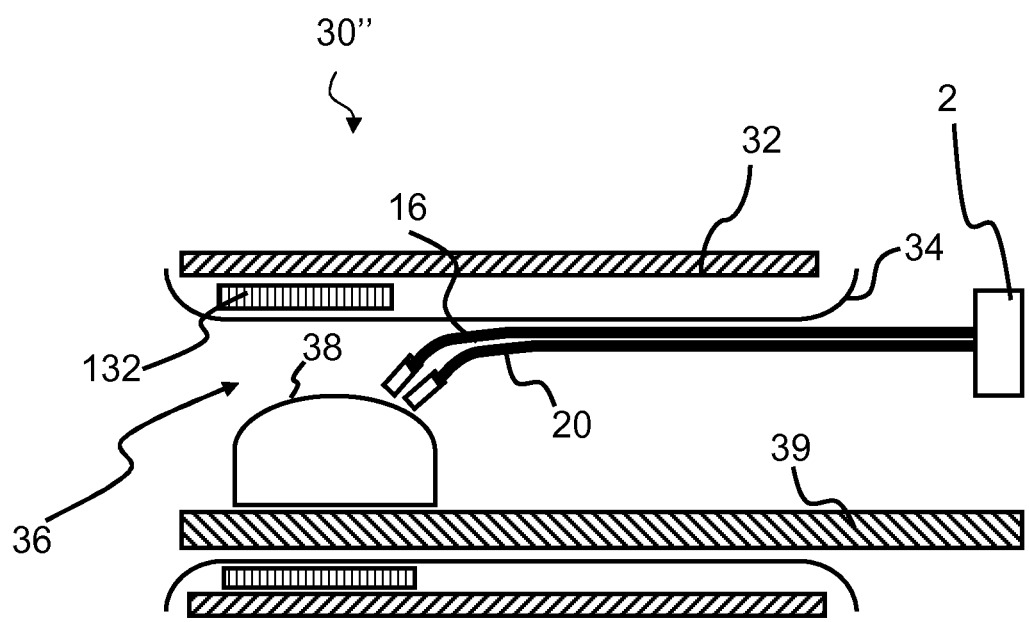

FIG. 15 schematically illustrates a medical scanner for use with the method and apparatus. The scanner 30" is a combined MR/PET scanner. Distal ends of the respective optical fibers 16, 20 are positioned inside the scanner borehole 36 for projecting and detecting pattern sequences on/from a surface region within the scanner borehole 36.

Figure 16:
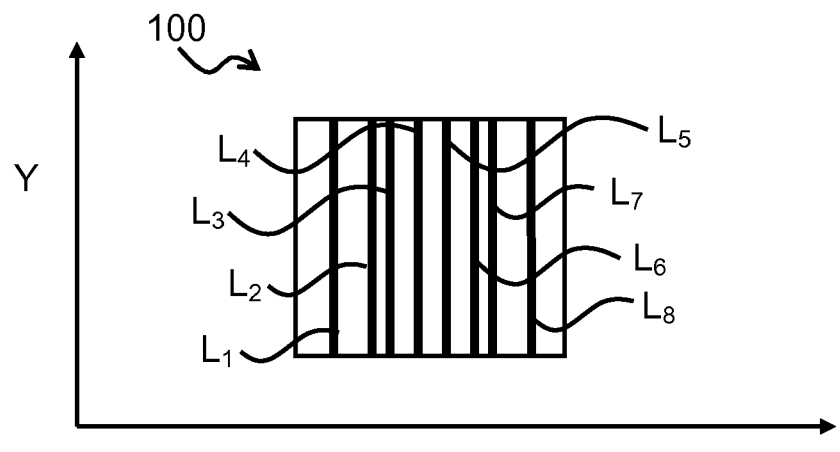
FIGS. 16-18 illustrates exemplary patterns of a pattern sequence.

FIG. 16 illustrates an exemplary pattern 100, such as a desired detected pattern P', a projected pattern P and/or a detected pattern P'. The pattern 100 comprises eight parallel straight line segments $L_1, \ldots, L_8$ parallel to the second axis X. At least some of the line segments vary in width, and the distance between line segments may be constant or vary. Pattern subregions corresponding to the eyes or other regions of a subject may be masked out, see e.g. FIG. 12C and FIG. 12D.

Figure 17:
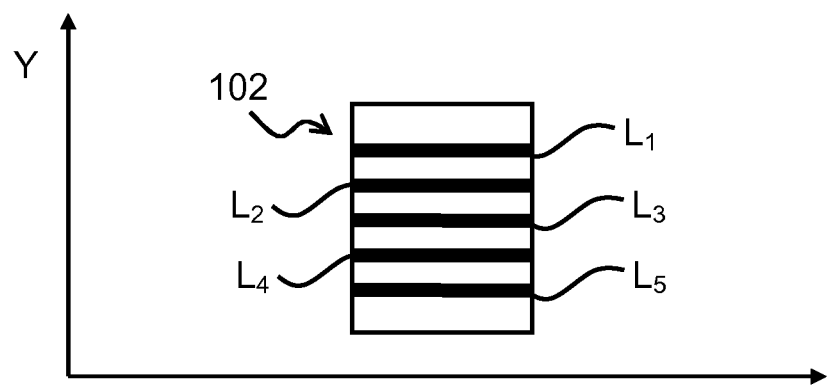

FIG. 17 illustrates an exemplary pattern 102, such as a desired detected pattern P', a projected pattern P and/or a detected pattern P'. The pattern 102 comprises five equidistant parallel straight line segments $L_1, \ldots, L_5$ parallel to the first axis X and having the same width. Pattern subregions corresponding to the eyes or other regions of a subject may be masked out, see e.g. FIG. 12C and FIG. 12D.

Figure 18:
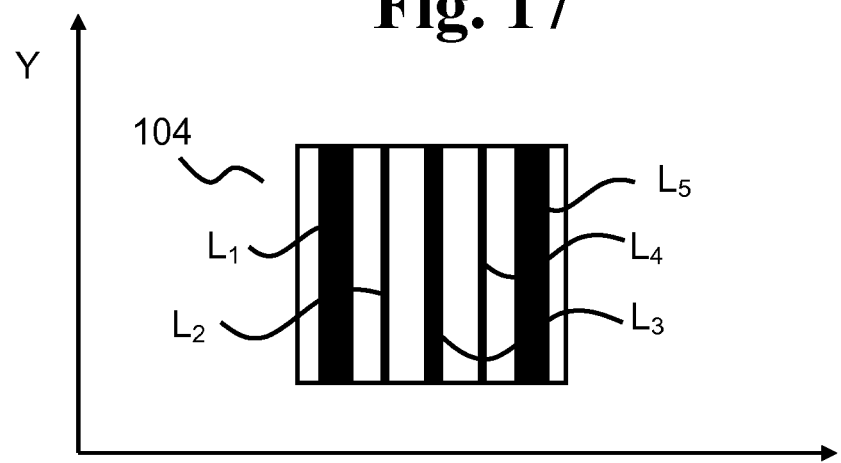

FIG. 18 illustrates an exemplary pattern 104, such as a desired detected pattern P', a projected pattern P and/or a detected pattern P'. The pattern 104 comprises five parallel straight line segments $L_1, \ldots, L_5$ parallel to the second axis Y. A first set of line segments $L_1$ and $L_5$ have the same width and a second set of line segments $L_2$ and $L_4$ have the same width different from the width of the first set of line segments. Pattern subregions corresponding to the eyes or other regions of a subject may be masked out, see e.g. FIG. 12C and FIG. 12D.

It is to be noted that one or more of the line segments of a pattern e.g. as illustrated in FIGS. 16-19 may be curved. A curved line segment of a projected pattern may appear as a straight line segment in the detected pattern due to the curvature of the surface region of the subject as further illustrated below.

Figure 19:
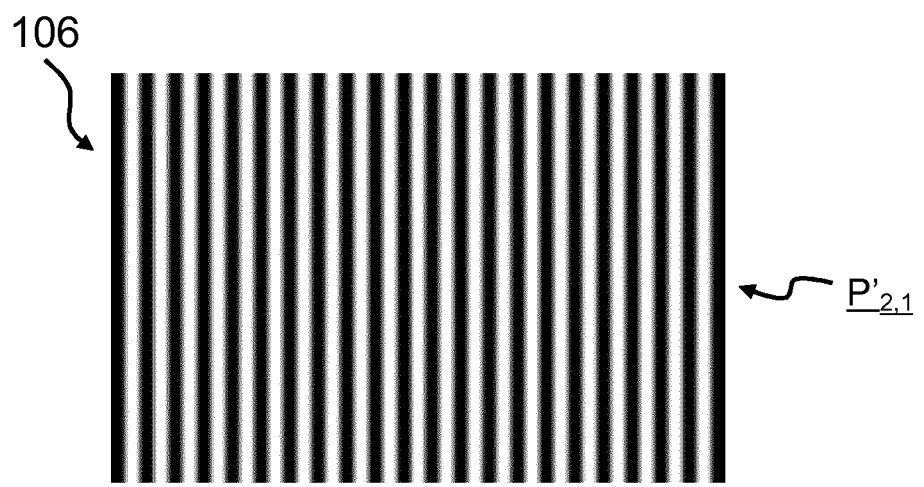
FIGS. 19-20 illustrates a desired detected pattern and a projected pattern derived therefrom, respectively.
Figure 20:
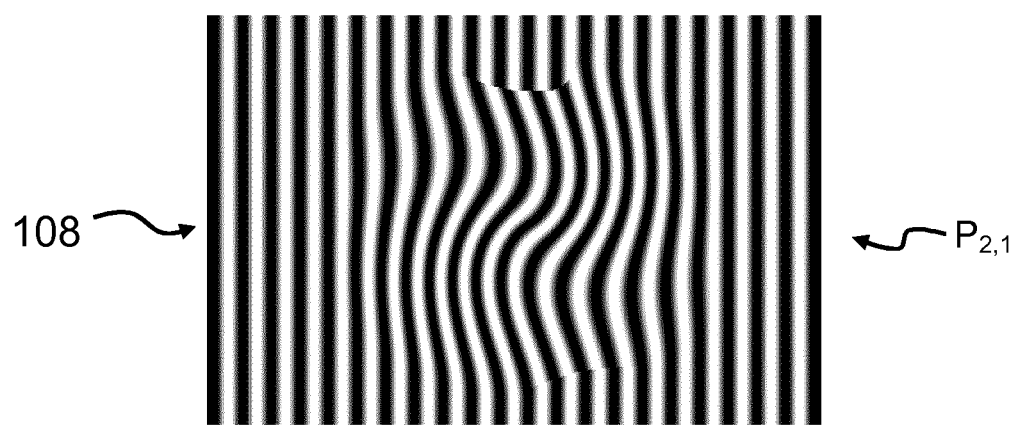

FIG. 19 illustrates an exemplary desired detected second primary pattern (P'$_{2,1}$) 106. FIG. 20 illustrates the corresponding second primary pattern (P$_{2,1}$) 108 determined as a function of optionally the projected first pattern sequence (S1) or pattern(s) thereof, the detected first pattern sequence (S1') or pattern(s) thereof, and the desired detected second primary pattern (P'$_{2,1}$) 106.

It should be noted that in addition to the exemplary embodiments of the invention shown in the accompanying drawings, the invention may be embodied in different forms and should not be construed as limited to the embodiments set forth herein. Rather, these embodiments are provided so that this disclosure will be thorough and complete, and will fully convey the concept of the invention to those skilled in the art.

LIST OF REFERENCES

2 Apparatus
4 Housing
6 Control unit
8 Light projector
10 Light source
12 Light modulator 14 First camera
16 First optical fibers
17 Proximal ends of first optical fibers
18 First optical coupler
20 Second optical fibers
21 Proximal ends of second optical fibers
22 Second optical coupler
24 Memory
26 User interface
30, 30', 30" Medical scanner
32 Magnet
34 Scanner housing
36 Scanner borehole
38 Head coil
39 Scanner bed
40 Subject
42 Distal ends of first optical fibers
44 Distal ends of second optical fibers
50, 50' Method for motion tracking of a subject in medical brain imaging
52 Provide light projector and first camera
54 Project first pattern sequence
56 Detect first pattern sequence
58 Determine second pattern sequence/new pattern sequence
60 Project second pattern sequence
62 Detect second pattern sequence
64 Determine motion correction parameters
65 Recalculation necessary?
80 Subregion of second pattern
82 Pixel
84 Pixel
86 Subregion of pattern
88 Subregion of pattern
90 Subregion of pattern
92 Subregion of pattern
94 Processor
96 Interface
98 Internal memory
100 Pattern of a projected pattern P, a detected pattern P' and/or desired detected pattern P'
102 Pattern of a projected pattern P, a detected pattern P' and/or desired detected pattern P'
104 Pattern of a projected pattern P, a detected pattern P' and/or desired detected pattern P'
106 Exemplary desired detected pattern P'
108 Exemplary projected pattern P
132 Detector ring
L line segment

The invention claimed is:

1. A method for motion tracking of a subject in medical brain imaging, the method comprising:
providing a light projector and a first camera;
projecting a first pattern sequence onto a surface region covering a curvature of a nasal bridge of the subject with the light projector, wherein the subject is positioned in a scanner borehole of a medical scanner, the first pattern sequence comprising a first primary pattern and a first secondary pattern;
detecting the projected first pattern sequence with the first camera;
determining a second pattern sequence comprising a second primary pattern based on first position parameters obtained from the detected first pattern sequence;
projecting the second pattern sequence onto a surface region covering the curvature of the nasal bridge of the subject with the light projector;
detecting the projected second pattern sequence with the first camera; and
determining motion tracking parameters based on second position parameters obtained from the detected second pattern sequence by:
(i) generating a 3D point cloud representation of the surface region covering the curvature of the nasal bridge with the second position parameters,
(ii) generating a 3D point cloud representation for a reference surface based on default position parameters of the subject, and
(iii) calculating the motion tracking parameters using image data obtained from the 3D point cloud representation generated in steps (i) and (ii).

2. Method according to claim 1, wherein the second pattern sequence comprises a second secondary pattern.

3. Method according to claim 1, wherein projection of the first pattern sequence and detection of the projected first pattern sequence is repeated at least once and wherein the second pattern sequence is based on the repeated first pattern sequence.

4. Method according to claim 1, wherein the surface region has an area in the range from 1 $cm^2$ to 500 $cm^2$.

5. Method according to claim 1, wherein the first primary pattern comprises light at a first wavelength and the first secondary pattern comprises light at a second wavelength.

6. Method according to claim 1, wherein determining the second pattern sequence comprises determining second pattern(s) such that projection of light onto the eye region of the subject during projection of the second pattern sequence is limited or substantially eliminated.

7. Method according to claim 1, the method comprising sending the motion tracking parameters to the medical scanner or a control unit for motion correction of the scanning images.

8. Method according to claim 1, wherein providing a light projector and a first camera comprises providing first optical fibers having proximal ends and distal ends, wherein the proximal ends of the first optical fibers are optically coupled to the light projector and the distal ends of the first optical fibers are positioned within the scanner borehole, and wherein the first and second pattern sequences are projected through the first optical fibers.

9. Method according to claim 1, wherein providing a light projector and a first camera comprises providing second optical fibers having proximal ends and distal ends, wherein the proximal ends of the second optical fibers are optically coupled to the first camera and the distal ends of the second optical fibers are positioned within the scanner borehole, and wherein the projected first and/or second pattern sequences are detected through the second optical fibers.

10. Method according to claim 1, wherein the reference surface is based on calculation of default position parameters of the subject.

11. Method according to claim 10, wherein the default position parameters are calculated based on the detected first pattern sequence.

12. Method according to claim 1, wherein the second pattern sequence excludes one or more subregions from the first pattern sequence.

13. Method according to claim 1, wherein the determining of the second pattern sequence comprising the second primary pattern is based on position parameters of the detected first pattern sequence.

14. Method according to claim 13, wherein the determining the second pattern sequence comprises determining second pattern(s) such that projection of light onto an eye region of the subject during projection of the second pattern sequence is limited or substantially eliminated.

* * * * *